United States Patent [19]

Hirai

[11] Patent Number: 5,015,442
[45] Date of Patent: May 14, 1991

[54] STERILIZING/DEODORIZING APPARATUS

[75] Inventor: Yoichi Hirai, Aichi, Japan

[73] Assignee: Tokai Kogyo Co., Ltd., Aichi, Japan

[21] Appl. No.: 315,529

[22] Filed: Feb. 24, 1989

[30] Foreign Application Priority Data

Feb. 29, 1988 [JP] Japan .................................. 63-44523

[51] Int. Cl.⁵ .............................................. A61L 9/20
[52] U.S. Cl. .................... 422/121; 422/122; 422/124; 422/186.3
[58] Field of Search ................ 422/4, 5, 24, 121, 124, 422/186.07, 186.08, 186.3, 186.14, 122

[56] References Cited

U.S. PATENT DOCUMENTS

| | | |
|---|---|---|
| 1,932,379 | 8/1931 | Ballentine ................................ 422/4 |
| 2,638,644 | 5/1953 | Rauhut ............................... 422/5 X |
| 3,442,602 | 5/1969 | Diehl ....................................... 422/4 |
| 3,576,593 | 4/1971 | Cicirello ............................ 422/24 X |
| 4,210,429 | 7/1980 | Golstein ............................ 422/24 X |
| 4,309,388 | 1/1982 | Tenney et al. ..................... 422/30 X |
| 4,343,765 | 8/1982 | Elston et al. ....................... 422/4 X |
| 4,348,360 | 9/1982 | Chang et al. ..................... 422/122 |
| 4,370,301 | 1/1983 | Doi et al. ............................ 422/4 X |

Primary Examiner—David L. Lacey
Assistant Examiner—Jeffrey R. Snay
Attorney, Agent, or Firm—Flynn, Thiel, Boutell & Tanis

[57] ABSTRACT

A sterilizing/deodorizing apparatus having a fan for creating an air flow in one direction in a box-like body. The body has divided air passages, one of the air passages having an ozonizer and an air-permeable ozone-decomposing catalyzer, and the other air passage simply allowing untreated air to flow therethrough.

3 Claims, 4 Drawing Sheets

STERILIZING/DEODORIZING APPARATUS

FIELD OF THE INVENTION

The present invention relates to a sterilizing/deodorizing apparatus for efficiently cleaning air containing bad-smelling components and floating germs.

BACKGROUND OF THE INVENTION

In an apparatus intended for cleaning air in a room for the purpose of dust-collecting, deodorizing, sterilizing, etc., not only efficiency but largeness of volume of treated air is required. As the volume of the treated air is increased, the air in a room can be circulated to a larger degree, thereby cleaning the air in a room as a whole within a shorter period of time. Even if an apparatus itself is efficient, if the apparatus is put in a room the volume of which is beyond the possible treating capacity of the apparatus, the circulation of the air within the room may not be fully effected, thereby requiring a longer time to clean the whole air in the room.

Recently, sterilization and deodorization using ozone has been highlighted. However, since ozone is harmful to the human body, such an apparatus must have an ozone removing means before exhausting the treated air. Conventional systems employ layers of activated carbon or catalyzers provided in the air passage to remove ozone, thus giving rise to a larger pressure drop (loss) at those layers. The resultant drawbacks are:

(1) Since the air in a room may not be stirred, the effect of dust-collecting, deodorization and sterilization is concentrated in the vicinity of the apparatus. Consequently, such an apparatus is not suitable to be used in a spacious room.
(2) The types of available fans are limited. For example, cross flow fans which are capable of generating large quantity of air flow with a relatively low noise may not be used.
(3) If the thickness of the layers for removing ozone is reduced to lessen the pressure drop, ozone removal may not be fully effected.
(4) Therefore, the apparatus inevitably becomes large in size in order to remove ozone completely and to increase the amount of the treated air.

SUMMARY OF THE INVENTION

The present invention is a sterilizing/deodorizing apparatus comprising a means for creating an air flow in one direction in a box-like body, said body having divided air passages, one of said air passages having an ozonizer and an air-permeable ozone-decomposing catalyzer, and the other of said air passages simply allowing untreated air to flow therethrough.

The air to be treated containing floating germs or bad-smelling components introduced into the apparatus by the flow creating means, such as a cross flow fan, is introduced into a passage provided with an ozonizer and an air-permeable ozone-decomposing catalyzer; and another passage which allows the untreated air to simply pass therethrough.

In one of the two passages, ozone is generated from oxygen in the air by means of the ozonizer to fill the passage with ozone. The ozone partly decomposes the bad-smelling components contained in the air. If the ozonizer is an ultraviolet-ray lamp radiating ultraviolet rays having an effective principal wavelength of 185 nm, ozone may be generated according to the following formula:

$$O_2 + h\nu_1 \rightarrow O + O \tag{I}$$

$$O_2 + O + M \rightarrow O_3 + M \tag{II}$$

where M represents a substance such as O, N, etc.

Simultaneously, sterilization by means of the ultraviolet rays takes place.

The air full of ozone is then introduced into the catalyzer for decomposing the ozone; and the ozone may be decomposed according to the following formula:

$$O_3 + T \rightarrow O_2 + O + T \tag{III}$$

where T represents a catalyst.

O is the so-called "nascent" oxygen having a high oxidizing power so as to sterilize the floating germs contained in the treated air and decompose the bad-smelling components.

In the next place, the air passing the catalyzer, having been subjected to the sterilization and deodorization, and the untreated air which simply passed through the other passage, join to be exhausted out of the apparatus.

An ultraviolet ray lamp may be provided where the two flows join together to sterilize the floating germs in the air. If this lamp is an ultraviolet ray lamp radiating ultraviolet rays having an effective principal wavelength of 254 nm, the ozone may be decomposed according to the following formula:

$$O_3 + H\nu_2 \rightarrow O_2 + O \tag{IV}$$

The ultraviolet ray lamp radiates the whole treated air to sterilize it, and prevents the ozone from going out of the apparatus without being decomposed.

Most of the air is exhausted out of the apparatus through the other passage which serves as a bypass because of the pressure drop, so that the circulation of the air within the room in which the apparatus has been installed may be promoted so as to increase the amount of treated air.

An air-flow adjusting means may preferably be provided in at least one of the air passages to adjust the flow of air through the bypass according to the volume of the room. By operating said flow adjusting means intermittently, the amount of air flowing through the two passages may be changed at a predetermined interval, thus improving the efficiency of sterilization/deodorization of the whole room in addition to the increased circulation of the air within the room due to the air passing through the bypass.

Furthermore, by providing an ozonizing ultraviolet ray lamp in the vicinity of the entrance of the air flow, namely, in the vicinity of the division of the flow into the two passages, it is possible to let the treated air contain ozone. Although ozone is harmful to the human body, the thus-constituted apparatus may be utilized at night or at those places where there is not much human traffic or occupancy, thus sterilizing the whole room by ozone. Thereafter, the ozonizing ultraviolet ray lamp may be restored to the normal position, namely, immediately downstream of the ozone decomposing catalyzer layer to remove the ozone by degrees as a result of the continued operation of the apparatus.

DETAILED DESCRIPTION

Figure 1:
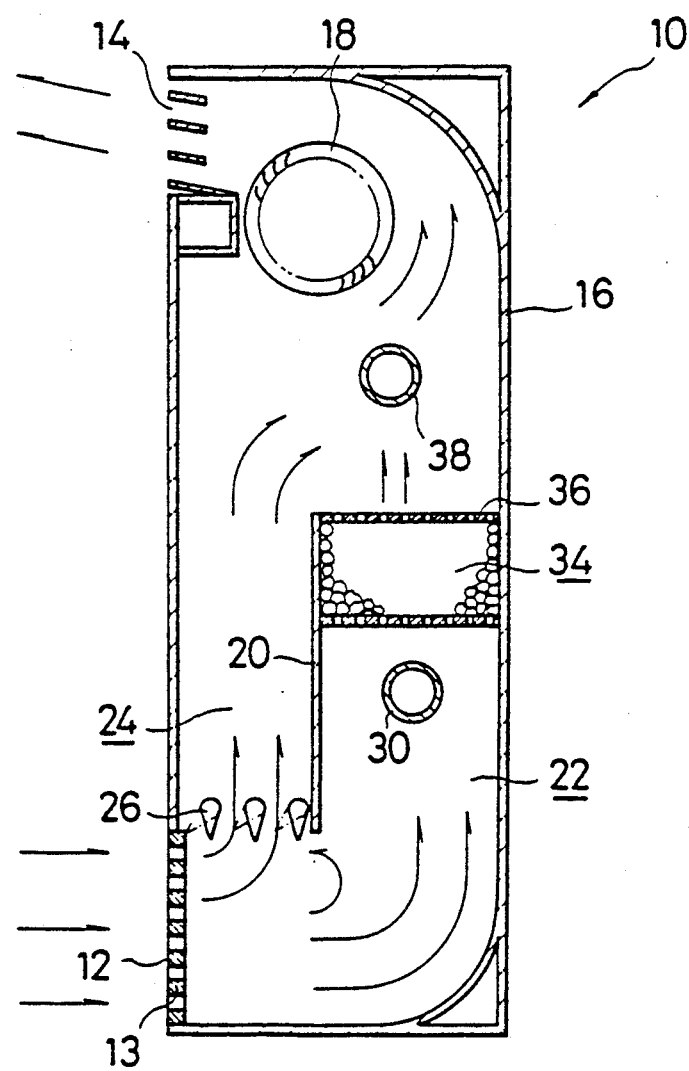
FIG. 1 is a sectional view of a first embodiment in which a flow adjusting means is open.
Figure 2:
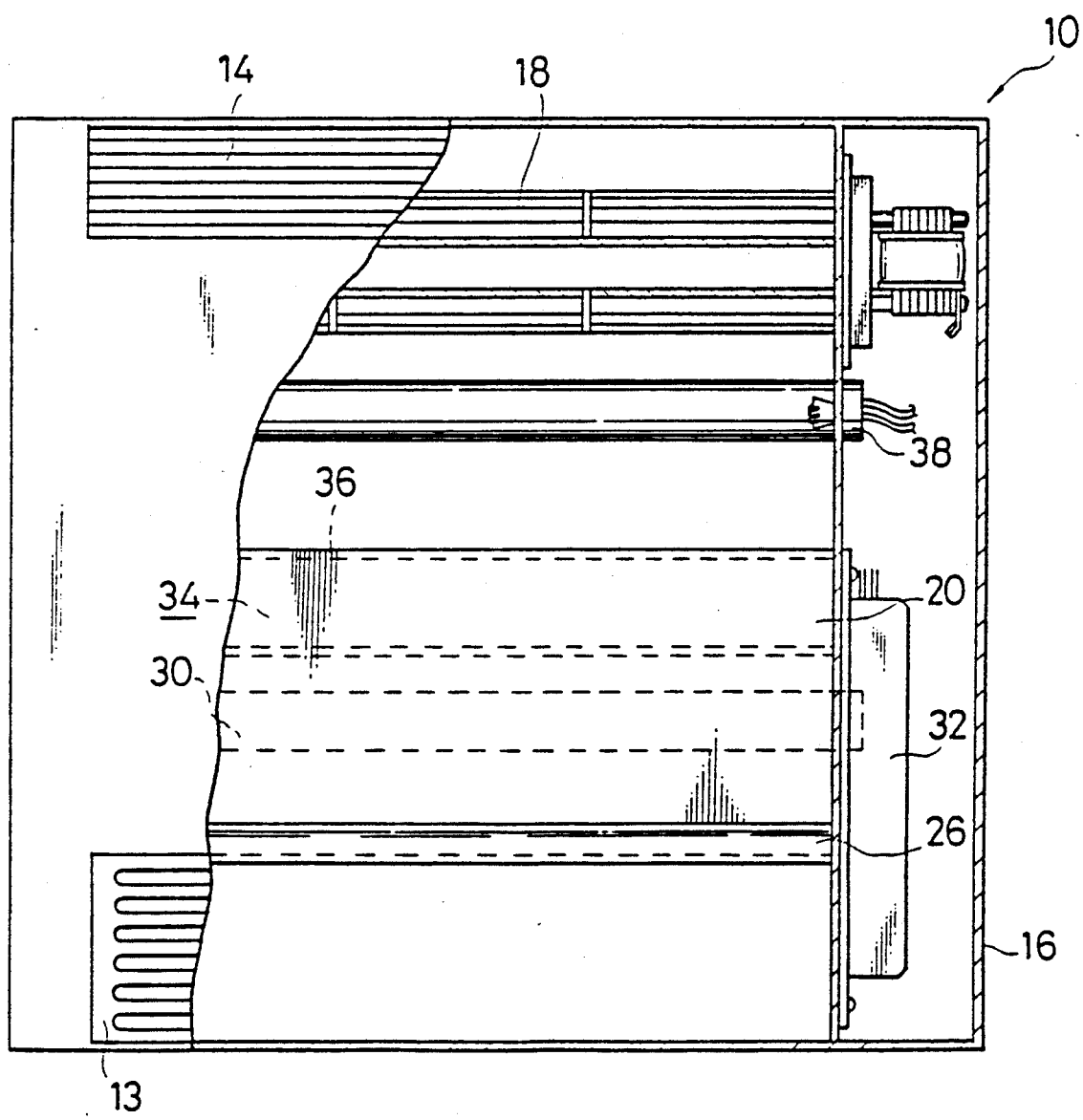
FIG. 2 is a partly broken away front view.
Figure 3:
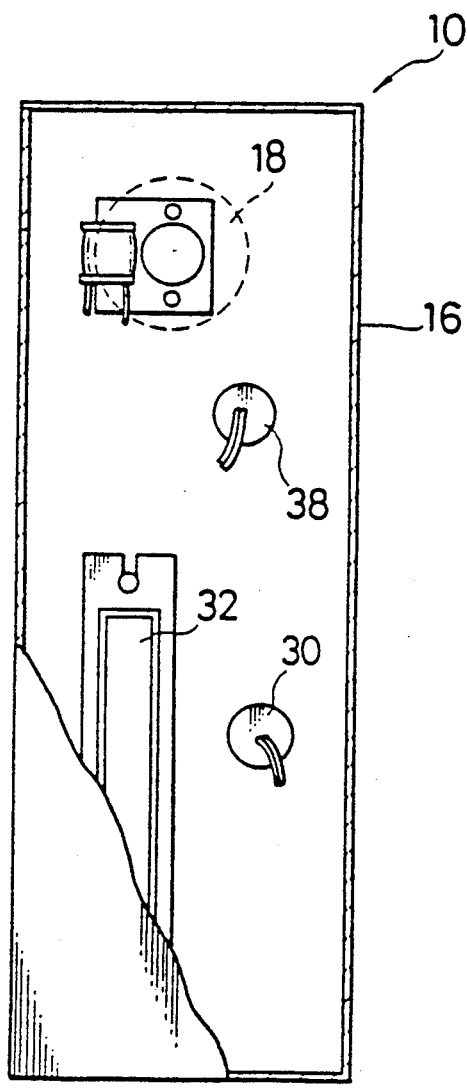
FIG. 3 is a partly broken away side view.

The sterilizing/deodorizing apparatus 10 of FIGS. 1 and 2 comprises a box-like body 16 having an inlet 12, outlet 14, two air passages 22, 24 and a fan 18 to create flow of air in said passages. At the inlet 12, a pre-filter 13 is provided for collecting relatively large sized dusts, etc. The introduced air first passes the pre-filter 13 and is further introduced into the parallel passages 22 and 24 divided by means of a partition wall 20.

The pre-filter 13 comprises, for example, a net-like structure of relatively large mesh; and functions to catch relatively large-sized dust particles in the air, such as waste threads, plumes, etc.

At the entrance of the bypass passage 24 through which untreated air simply passes, an air flow adjusting means 26 is provided to enable adjustment in the total quantity of air to be treated by the apparatus, and in the ratio of the flow rates in the deodorizing/sterilizing passage 22 and the bypass passage 24.

Within the deodorizing/sterilizing passage 22, an ultraviolet ray lamp 30 for generating principally ultraviolet rays of an effective wavelength of 185 nm from the oxygen in the air and an ozone decomposing catalyzer layer 34 are disposed in series in the direction of air flow. The numeral 32 denotes a stabilizer for the ultraviolet ray lamp.

Within the ozone decomposing catalyzer 34, a layer of an ozone decomposing catalyst is accommodated in an air-permeable container 36. Examples of such structures are, an air-permeable container containing particulate catalysts for decomposing ozone, or a three-dimensional structure packed with ozone decomposing catalysts.

As the catalyst, transition metal oxide such as nickel oxide, copper oxide or the like, precious metal such as platinum or the like, or a mixture of these materials, may be suitably used.

The ozonizing ultraviolet ray lamp 30 is adapted to be moved to the vicinity of the dividing point of the flow (that is, the entrance end of passage 22) by means of an advancing means (not shown).

As ozonizing means, other means utilizing electric discharge may also be employed.

As a fan 18, which is to generate air flow from the inlet 12 toward the outlet 14, a so-called cross flow fan is preferably used since it is relatively compact with less noise having larger capacity for creating winds, although other types of fans may also be used.

Furthermore, between the downstream joining point of the two flows and the fan 18, a sterilizing ultraviolet ray lamp 38 (effective principal wavelength of 254 nm) is disposed in such a position as to radiate the upper portion of the catalyzer layer 34.

Figure 4:
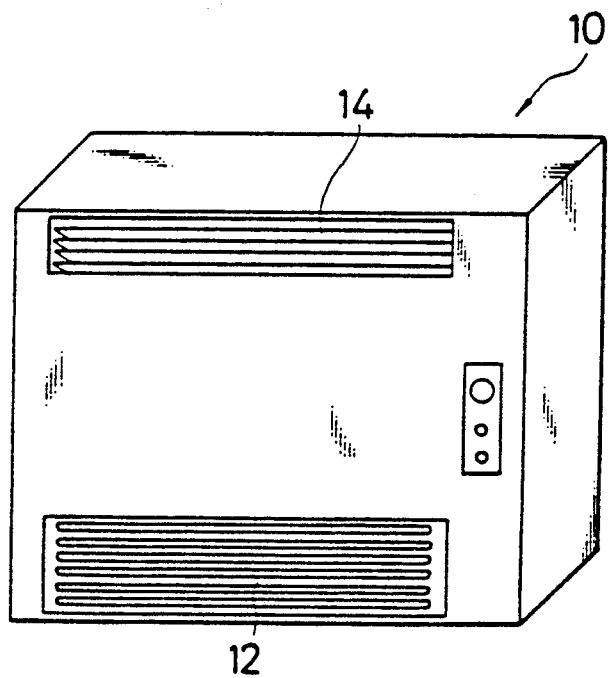
FIG. 4 is a perspective overall view.

The overall appearance of the apparatus is as shown in FIG. 4.

In order to start the operation, the ozonizing ultraviolet ray lamp 30 as well as the sterilizing ultraviolet ray lamp 38 are lit; the fan 18 is driven; and air is introduced into the box-like body 16 through the pre-filter 13.

The thus-introduced air is divided into one flow passing through the sterilizing/deodorizing passage 22 and another flow passing through the bypass passage 24. The flow rate in the sterilizing/deodorizing passage 22 may be adjusted by means of the flow adjusting means 26 provided within the bypass 24. The flow adjusting means 26 may instead be provided in the passage 22 if desired.

Figure 5:
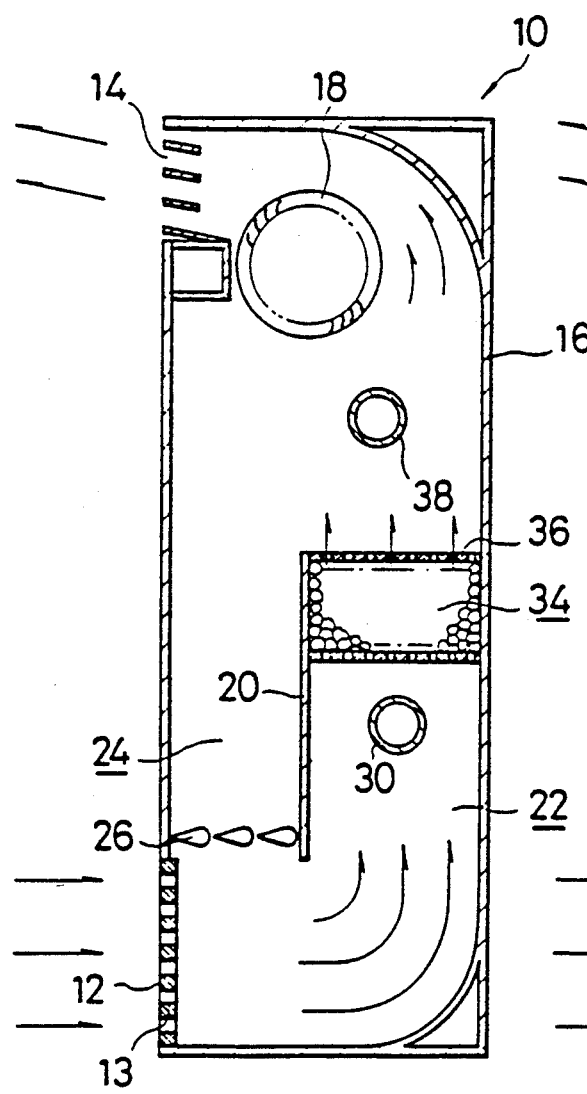
FIG. 5 is a sectional view in which the flow adjusting means is closed.

In case the flow adjusting means 26 is closed as shown in FIG. 5, all the introduced air must pass through the sterilizing/deodorizing passage 22. Since the ozone decomposing catalyst layer 34 is provided within the sterilizing/deodorizing passage 22, the pressure drop across the layer 34 is at a maximum and the amount of the treated air is at a minimum.

With respect to the air passing through the sterilizing/deodorizing passage 22, a first-step sterilization of the floating germs is conducted by means of the ultraviolet rays radiated by the ozonizing lamp 30 (effective wavelength 185 nm). Simultaneously, ozone is generated out of the oxygen atoms in the air in the vicinity of the lamp 30 in accordance with the formula (I) and (II) as mentioned above. As is well known, ozone is possessed of a high oxidizing power to partly decompose the bad-smelling components.

In the next place, the ozone is decomposed to oxygen (O) by the catalyzer layer 34 in accordance with the formula (III) and by the sterilizing ultraviolet ray lamp 38 radiating ultraviolet rays of wavelength of 254 nm in accordance with formula (IV), respectively. A secondary sterilization and decomposition (by oxidization) of bad-smelling/noxious components take place as they mix with the (nascent) oxygen atoms thus generated having even stronger oxidizing power. The sterilizing ultraviolet ray lamp 38 decomposes the ozone only when there is residual ozone.

The thus processed air which has been made unharmful is exhausted out of the apparatus 10 through the outlet 14 by means of the fan 18.

Next, in case the flow adjusting means 26 is fully open (see FIG. 1), most of the treated air introduced into the apparatus 10 goes into the bypass 24 due to the substantial difference in the pressure drop between the two passages 22 and 24. In this case, the quantity of the air to be treated by the apparatus may be substantially increased compared with the case in which the flow adjusting means 26 is closed.

The air which passes through the bypass 24 is subjected to sterilization by the ultraviolet rays radiated by the sterilizing ultraviolet ray lamp 38 located downstream of where the two flows join. Furthermore, a part of the treated air passes through the sterilizing/deodorizing passage 22 and is subjected to sterilization/deodorization by means of ozone.

In case the flow adjusting means 26 is open, efficiency of sterilization/deodorization will deteriorate compared with the case where it is closed; however, circulation of air within a room may be promoted because the amount of treatable air substantially increases.

By setting the position of the flow adjusting means 26 between the fully open and closed positions, the flow rate in the sterilizing/deodorizing passage 22 may be controlled. The flow adjusting means 26 may be manipulated intermittently. Moreover, the operation may be adjusted according to the size of a room. Namely, if the volume of a room is relatively small, the apparatus may be operated with the flow adjusting means 26 fully closed or with a relatively short time of the opening condition thereof, thereby enabling a highly efficient sterilization/deodorization attainable owing to the closing of the flow adjusting means.

On the other hand, in case the volume of a room is relatively large, the apparatus may be operated with the flow adjusting means 26 open for longer intervals, thus fully circulating the air within the room. In this case, the efficiency of sterilization/deodorization will be lower; but the time required to circulate the whole air in the room may be shortened; and consequently the overall time required to treat the air within the room may be shortened.

Figure 6:
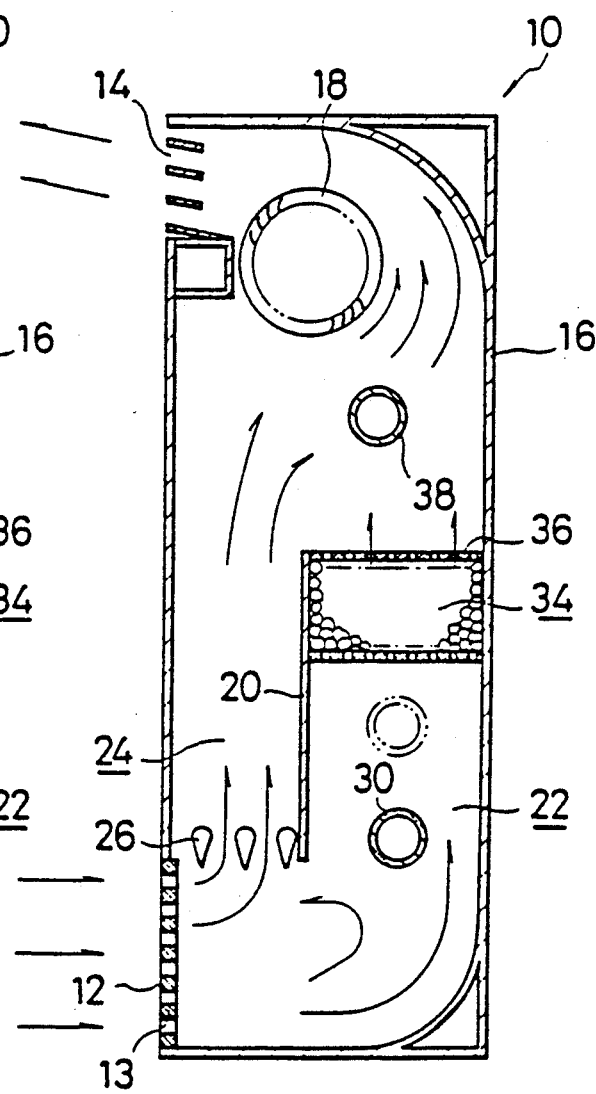
FIG. 6 is a sectional view in which the flow adjusting means is open, and the ozonizing ultraviolet ray lamp is located in the vicinity of the air inlet.

In addition, by adjustably setting the location of the ozonizing ultraviolet ray lamp 30, it becomes possible to intentionally include a predetermined amount of ozone in the exhausted air. Namely, the movement of the ozonizing ultraviolet ray lamp 30 toward the entrance of the passages 22, 24 (see FIG. 6) will allow a part of the ozone generated in the vicinity of the lamp 30 to be exhausted out of the apparatus through the bypass 24. The concentration of the ozone can be roughly controlled by the position of the lamp 30. Thus, a whole room may be ozone-sterilized, for example, during the night when there is no traffic (i.e., no occupancy). Thereafter, the ozonizing ultraviolet ray lamp 30 may be restored to the original position, thereby removing ozone by degrees.

According to the present invention as explained above, it is possible to shorten the time required to sterilize/deodorize air within a room owing to the effective circulation of a larger quantity of the treated air. Moreover, a cross flow fan, which is unsuitable when there is a large pressure drop, may be employed, which enables the apparatus to be compact and to be operable with a lower noise. Also, the apparatus is capable of treating a larger quantity of air.

In addition, by adjusting the degree of opening of the flow adjusting means, a restricted rate of flow useful for sterilization/deodorization or a larger rate of flow for circulating air in a room may be selectively obtained. Moreover, by adjusting the change-over of the flow adjusting means in terms of time, treatment of air may be made in accordance with the volume of a room in a shorter period of time. It is of course possible to carry out highly efficient sterilization/deodorization.

Furthermore, by changing the location of an ozonizing ultraviolet ray lamp 30, it becomes possible to include ozone having a predetermined concentration in the exhaust air, which enables ozone-sterilization of a whole room.

To permit adjustment in the positioning of the ultraviolet ray lamp 30, this lamp 30 may be mounted on any type of support structure which is positioned internally of the body 10 and can be selectively manually moved vertically thereof to hence change the position of the lamp 30. For example, the ends of the lamp could be supported by a channel or yoke structure, with the latter in turn being vertically slidably movable within the box-like body 16 to hence enable movement of the lamp 30 between the two positions illustrated by FIG. 6 Such support can be suitably controlled and selectively locked in any desired position by use of conventional structure, such as conventional manually-actuated locking knobs or the like. It will be recognized that numerous conventional structures can be provided for adjustably movably supporting the lamp 30.

Although a particular preferred embodiment of the invention has been disclosed in detail for illustrative purposes, it will be recognized that variations or modifications of the disclosed apparatus, including the rearrangement of parts, lie within the scope of the present invention.

I claim:

1. A sterilizing/deodorizing apparatus for treating air, comprising:
   a substantially hollow box-like body defining therein first and second air receiving chambers;
   an air inlet formed in said body in communication with said first chamber to permit untreated air to be supplied thereto;
   an air outlet provided in said body in communication with said second chamber to permit air to be discharged therefrom;
   divider wall means mounted within said body for defining generally elongate first and second air passages which are isolated from one another and each of which has inlet and outlet ends providing communication with said first and second chambers, respectively;
   means positioned within said body for creating air flow through said body from said inlet to said outlet;
   flow adjusting means provided in said second passage for adjustably controlling the ratio of flows through said first and second passages by controlling the amount of flow through said second passage, said flow adjusting means being positioned adjacent the inlet end to said second passage;
   an ozone generating means disposed within said first passage for generating ozone in the air passing from said first chamber through said first passage to said second chamber, said ozone generating means comprising an ultraviolet ray lamp which radiated ultraviolet rays of a wavelength of about 185 nm;
   means movably supporting said lamp for movement between a first position wherein the lamp is disposed within said first passage at a substantial distance downstream from the inlet end thereof, and a second position wherein the lamp is disposed closely adjacent the inlet end to said first passage;
   an ozone-decomposing catalyzer disposed within said first passage downstream of said ozone generating means; and
   said second passage being free of air treating devices and being sized such that, when said second passage is fully open, most of the untreated air flowing through the inlet into said first chamber flows untreated through said second passage into said second chamber so as to bypass said first passage.

2. An apparatus according to claim 1, wherein said ozone-decomposing catalyzer extends transversely across said first passage adjacent the outlet end thereof so that all air flowing through said first passage must pass therethrough.

3. An apparatus according to claim 2, wherein a sterilizing ultraviolet ray lamp which radiates ultraviolet rays of a wavelength of about 254 nm is positioned within said second chamber.

* * * * *

UNITED STATES PATENT AND TRADEMARK OFFICE
CERTIFICATE OF CORRECTION

PATENT NO. : 5 015 442
DATED : May 14, 1991
INVENTOR(S) : Yoichi Hirai It is certified that error appears in the above-identified patent and that said Letters Patent is hereby corrected as shown below:

Column 6, line 41; change "radiated" to ---radiates---.

Signed and Sealed this

Twenty-eighth Day of December, 1993

Attest:

BRUCE LEHMAN

Attesting Officer

Commissioner of Patents and Trademarks